United States Patent [19]
Aebischer et al.

[11] Patent Number: 5,952,226
[45] Date of Patent: Sep. 14, 1999

[54] HYPOXIA RESPONSIVE EPO PRODUCING CELLS

[75] Inventors: Patrick Aebischer, Villette; Nicole Deglon, Curtilles; Etienne Regulier; Christopher Rinsch, both of Lausanne, all of Switzerland

[73] Assignee: Modex therapeutiques, Switzerland

[21] Appl. No.: 08/853,236

[22] Filed: May 9, 1997

Related U.S. Application Data

[62] Division of application No. 08/746,021, Nov. 5, 1996.
[51] Int. Cl.⁶ .................................................. C12N 25/85
[52] U.S. Cl. ........................... 435/354; 435/325; 435/366
[58] Field of Search .................................. 435/325, 366, 435/354

[56] References Cited

U.S. PATENT DOCUMENTS

| | | |
|---|---|---|
| 4,677,195 | 6/1987 | Hewick et al. . |
| 4,732,889 | 3/1988 | Cynshi et al. . |
| 4,745,099 | 5/1988 | Akamatsu et al. . |
| 4,835,260 | 5/1989 | Shoemaker . |
| 4,904,584 | 2/1990 | Shaw . |
| 4,954,437 | 9/1990 | Beck et al. . |
| 4,990,336 | 2/1991 | Silvestri et al. . |
| 5,013,718 | 5/1991 | Adamson et al. . |
| 5,032,507 | 7/1991 | Yu et al. . |
| 5,106,954 | 4/1992 | Fibi et al. . |
| 5,158,881 | 10/1992 | Aekischer et al. . |
| 5,166,322 | 11/1992 | Shaw et al. . |
| 5,188,828 | 2/1993 | Goldberg et al. . |
| 5,278,065 | 1/1994 | D'Andrea et al. . |
| 5,292,654 | 3/1994 | Yoshimura et al. . |
| 5,334,640 | 8/1994 | Desai et al. . |
| 5,354,934 | 10/1994 | Pitt et al. . |
| 5,378,808 | 1/1995 | D'Andrea et al. . |
| 5,416,071 | 5/1995 | Igari et al. . |
| 5,441,868 | 8/1995 | Lin . |
| 5,457,089 | 10/1995 | Fibi et al. . |
| 5,482,924 | 1/1996 | Royet et al. . |
| 5,518,730 | 5/1996 | Fuisz . |
| 5,541,155 | 7/1996 | Leone-Bay et al. . |
| 5,541,158 | 7/1996 | Vance et al. . |
| 5,543,441 | 8/1996 | Rhee et al. . |
| 5,547,933 | 8/1996 | Lin . |
| 5,548,064 | 8/1996 | Russell-Jones et al. . |
| 5,550,178 | 8/1996 | Desai et al. . |

FOREIGN PATENT DOCUMENTS

| | | |
|---|---|---|
| 0 148 605 | 7/1985 | European Pat. Off. . |
| 0 232 034 | 8/1987 | European Pat. Off. . |
| 0 236 059 | 9/1987 | European Pat. Off. . |
| 0 255 231 | 2/1988 | European Pat. Off. . |
| 0 267 678 | 5/1988 | European Pat. Off. . |
| 0 269 394 | 6/1988 | European Pat. Off. . |
| 0 286 439 | 10/1988 | European Pat. Off. . |
| 0 357 804 | 3/1990 | European Pat. Off. . |
| 0 409 113 | 1/1991 | European Pat. Off. . |
| 0 410 246 | 1/1991 | European Pat. Off. . |
| 0 411 678 | 2/1991 | European Pat. Off. . |
| 0 427 189 | 5/1991 | European Pat. Off. . |
| 0 428 267 | 5/1991 | European Pat. Off. . |
| 0 503 583 | 9/1992 | European Pat. Off. . |
| 0 513 738 | 11/1992 | European Pat. Off. . |
| 0 613 683 | 9/1994 | European Pat. Off. . |
| 0 640 619 | 3/1995 | European Pat. Off. . |
| 0 658 627 | 6/1995 | European Pat. Off. . |
| 0 668 351 | 8/1995 | European Pat. Off. . |
| 0 668 353 | 8/1995 | European Pat. Off. . |
| 0 668 354 | 8/1995 | European Pat. Off. . |
| WO 85/03079 | 7/1985 | WIPO . |
| WO 86/03520 | 6/1986 | WIPO . |
| WO 86/04068 | 7/1986 | WIPO . |
| WO 89/05824 | 6/1989 | WIPO . |
| WO 90/09166 | 8/1990 | WIPO . |
| WO 90/12874 | 11/1990 | WIPO . |
| WO 91/05867 | 5/1991 | WIPO . |
| WO-92/19195 | 9/1992 | WIPO . |
| WO 93/09222 | 5/1993 | WIPO . |
| WO 93/21266 | 10/1993 | WIPO . |
| WO 93/23013 | 11/1993 | WIPO . |
| WO 93/25221 | 12/1993 | WIPO . |
| WO 94/24160 | 10/1994 | WIPO . |
| WO 94/24298 | 10/1994 | WIPO . |
| WO 94/25055 | 11/1994 | WIPO . |
| WO 94/29442 | 12/1994 | WIPO . |
| WO 95/04521 | 2/1995 | WIPO . |
| WO 95/13376 | 5/1995 | WIPO . |
| WO 95/14785 | 6/1995 | WIPO . |
| WO 95/21927 | 8/1995 | WIPO . |
| WO 95/27512 | 10/1995 | WIPO . |
| WO 95/29664 | 11/1995 | WIPO . |
| WO 96/14081 | 5/1996 | WIPO . |
| WO 96/19573 | 6/1996 | WIPO . |
| WO-96/40871 | 12/1996 | WIPO . |

OTHER PUBLICATIONS

Hamamori et al. Human Gene Therapy. vol. 5: 1349–1356 Nov. 1994.

Firth et al., Proc. Natl. Acad. Sci. USA, vol. 91: 6496–6500 Jul. 1994.

Goldberg et al., 1987 "The regulated expression of erythropoietin by two human hepatoma cell lines", PNAS 84:7972–7976.

Madan et al., 1993, "A 24–base–pair sequence 3' to the human erythropoietin gene contains a hypoxia–responsive transcriptional enhancer", PNAS 90:3928–3932.

Beck et al., 1993, "Characterization of Hypoxia–Responsive Enhancer in the Human Erythropoietin Gene Shows Presence of Hypoxia–Inducible 120–Kd Nuclear DNA–Binding Protein in Erythropoietin–Producing and Nonproducing Cells", Blood 82:704–711.

Horri et al (May 1996) British J. Harmatology vol. 93 Suppl. 2: 307 Abstract 1166.

Wang et al. (1992) Biotechnol. Bioerg. vol. 40: 1115–1118.

*Primary Examiner*—Christina Y. Chan
*Assistant Examiner*—Patrick Nolan
*Attorney, Agent, or Firm*—Ivor R. Elrifi; Michel Morency; Mintz, Levin

[57] ABSTRACT

A device and method for delivery of EPO to a patient using an implanted device that continuously releases EPO.

2 Claims, 7 Drawing Sheets

HYPOXIA RESPONSIVE EPO PRODUCING CELLS

This is a division, of application Ser. No. 08/746,021, filed Nov. 5, 1996.

TECHNICAL FIELD OF THE INVENTION

This invention relates to devices and methods for delivery of erythropoietin ("EPO"), preferably using encapsulated EPO-secreting cells.

BACKGROUND OF THE INVENTION

Erythropoietin is an essential growth factor in the erythrocytic lineage. This glycoprotein hormone is secreted mainly in the kidney peritubular cells and in the fetal liver in response to hypoxia. Jelkman W, *Physiol Reviews* 72(2): 449 (1992). In addition, cobalt chloride also induces Epo production. Goldwasser E. et al, *Blood* 13: 55 (1958). Tissue hypoxia is the primary stimulus for production of erythropoietin which levels may rise to 10000 U/I plama in severe anemia as compared to the normal value of 5–20 U/I.

The injection of recombinant erythropoietin (EPO) is now widely used for long-term treatment of anemia associated with chronic renal failure, cancer and human immunodeficiency virus infections. Recombinant human erythropoietin (rhEPO) has revolutionised the treatment of anemia in patients on maintenance haemodialysis, abolishing the need for blood transfusions. Winearls CG et al., *Lancet* 2(8157): 1175 (1986); Gimenez LF et al., *Hematology/Oncology Clinics of North America* 8(5): 913 (1994).

The injection of rhEPO is widely used as a replacement therapy for anemic patients. In chronic renal failure, anemia results from a destruction of EPO-secreting cells. In chronic diseases, loss of EPO-secreting cells also occurs. Such diseases include inflammatory diseases (e.g., rheumatoid arthritis and cancers) or infectious diseases (e.g., AIDS).

Treatment is often performed as self-administered subcutaneous (s.c.) injection which is thought to be more effective than the intravenous (i.v.) route, although the bioavailability of rhEPO is low. Jensen JD et al., *Eur J Clin Pharmacol* 46: 333 (1994); Stockenhuber F et al., *Nephron* 59: 399 (1991.)

The ability to deliver this hormone by gene or cell therapy rather than by repeated injections could provide substantial clinical and economic benefits. In one embodiment we contemplate using genetically modified cells secreting high levels of human Epo.

Permanent in vivo delivery of EPO according to the devices and methods of this invention could provide great benefits in terms of cost and clinical procedures. The median weekly dose of EPO is about 150 U/kg, administered by one to three injections. The annual cost of treating a 70 kg man is about 10000 Swiss francs.

Implantation of polymer encapsulated EPO-secreting cells would abolish the need of repeated injections without affecting the biological efficacy of EPO in treatment of human hemoglobinopathies.

The cell therapy approach described here is expected to provide a convenient means for continuous delivery of EPO from a retrievable implant.

SUMMARY OF THE INVENTION

This invention provides a novel methods and devices for delivering EPO. In one embodiment, one or more tethered devices, each containing typically between $10^3$ and $10^8$ cells, preferably $10^5$ to $10^7$ cells, most preferably about $10^6$ genetically modified cells, surrounded by a semipermeable membrane, are implanted in the patient providing for continuous release of EPO. The dosage delivered can be varied, and is sufficient to produce a therapeutic effect. Further, preferably the encapsulated cells express hugh levels of EPO, and are hypoxia responsive, increasing expression of EPO under hypoxic conditions.

The semipermeable membrane prevents immunologic rejection of the cells and interposes a physical, preferably virally impermeable, barrier between cells and host. Moreover, the device and the cells it contains may be retrieved from the patient.

DETAILED DESCRIPTION OF THE INVENTION

Figure 1:
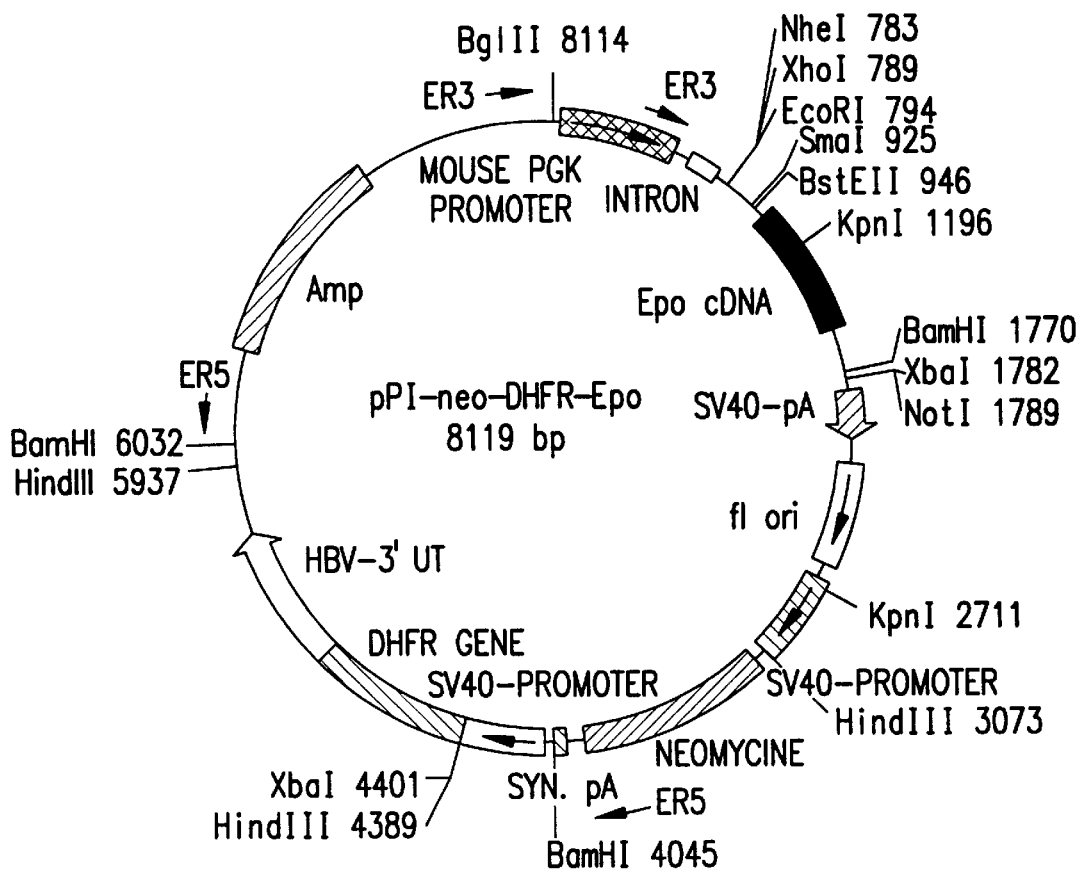
FIG. 1: Plasmid map of pPI-neo-DHFR-Epo vector containing the human EPO gene. Features of the vector include mouse PGK promoter (bp 14–523); chimeric intron (bp 588–720); T7 promoter (bp 765–783); EPO cDNA (bp 1077–1577); T3 promoter (bp 1796–1816); SV40 late polyadenylation signal (bp 1825–2046); phage f1 region (bp 2141–2596); SV40 enhancer and early promoter (bp 2660–3078); SV40 minimum origin of replication (bp 2976–3041); coding region of neomycin phosphotransferase (bp 3123–3917); synthetic polyadenylation signal (bp 3981–4029); SV40 promoter (bp 4050–4408); mutated DHFR gene Fnu4H1 (bp 4409–5059); HBV-3' UTR (bp 5060–5647); β-lactamase coding region (bp 6427–7287).

The devices and methods of this invention permit long-term delivery of high doses of rhEPO by implantation of polymer encapsulated cells genetically modified to secrete EPO into the serum. The provision of an encapsulating membrane of appropriate molecular weight cutoff shields the transplantated cells from the host immune system, thereby allowing the transplantation of cell lines across species. The dosage provided is sufficient to achieve a therapeutic effect in the patient. In one embodiment, living cells are encapsulated in one or more semipermeable polymer capsules and surgically inserted (under local anesthesia) into the patient.

This technique provides several advantages over other delivery routes:

(1) Drug can be delivered to the patient continuously thereby reducing fluctuations in dosage;

(2) If cells are viable for long periods of time (such as six months), patients will be inconvenienced only twice a year instead of three times weekly or every day with subcutaneous injections;

(3) Since viable cells continuously produce newly synthesized product, these cells should have advantages over pump delivery of drug stores, where drug is continuously degraded but not continuously replenished.

In one embodiment we contemplate cellular immunoisolation of Epo-producing allogenic or xenogenic cells surrounded by a selective membrane barrier for the treatment of human hemoglobinopathies. The implantation of these genetically modified encapsulated cell-lines is a convenient method to achieve permanent in vivo delivery of the hormone.

Cellular immunoisolation of EPO-producing allogenic or xenogenic cells provides a safe and simple therapy for patients suffering from anemia due to, e.g., chronic renal failure and beta-thalassemia. Capsules implanted subcutaneously can be removed and/or replaced easily. Second, a long-term correction of anemia by constant delivery of EPO would greatly enhance the patient's quality of life and decrease the cost of treatments.

The circulating form of human EPO is a 165 amino acid glycoprotein with an apparent molecular weight of about 30,000 daltons. The encapsulated cells of this invention produce EPO. Such cells may naturally produce EPO, or may be genetically engineered to do so. Such genetic engineering may involve transfection of cells with a vector containing a nucleotide sequence encoding EPO, preferably human EPO.

Alternatively, such genetic engineering may involvxe DNA targeting by homologous recombination to result in high level of expression an endogenous EPO gene. Such techniques are well Inown in the art. See WO 93/09222, incorporated herein by reference.

The human gene encoding EPO consists of five exons and five introns. The preferred EPO used in the present invention is the nucleotide and amino acid sequence encoding the human protein, such as described in U.S. Pat. No. 4,703,008 and 5,547,933 which are incorporated herein by reference. Modified, truncated, mutein and active fragment forms of EPO are well known and are contemplated by this invention. See, e.g., U.S. Pat. No. 5,457,089; 5,166,322; 4,835,260; and 5.106,954, all of which are specifically incorporated herein by reference.

In a preferred embodiment, full length recombinant human EPO (rhEPO) is used.

In vivo production of rat EPO in mice or rats have reported a consequent increase in hematocrit level. Naffakh N et al., $Proc\ Natl\ Acad\ Sci\ USA$ 92: 3194 (1995); Osborne WRA et al., $Proc\ Natl\ Acad\ Sci\ USA$ 92: 8055 (1995). Our approach, involving encapsulation of cells in a polymeric film with known physicochemical characteristics of molecular-weight-cut-off and chemical composition helps control the interaction between the host and the transplanted tissue. This effective immunoisolation of the transplanted tissue may render possible xenogenic transplantation in a broad spectrum of patients.

A gene of interest (i.e., a gene that encodes a suitable biologically active molecule, e.g., EPO) can be inserted into a cloning site of a suitable expression vector by using standard techniques. It will be appreciated that more than one gene may be inserted into a suitable expression vector. These techniques are well known to those skilled in the art.

The expression vector containing the gene of interest may then be used to transfect the desired cell line. Standard transfection techniques such as calcium phosphate co-precipitation, DEAE-dextran transfection or electroporation may be utilized. Commercially available mammalian transfection kits may be purchased from e.g., Stratagene.

A wide variety of host/expression vector combinations may be used to express the gene encoding EPO, or other biologically active molecule of interest.

Suitable promoters include, for example, the early and late promoters of SV40 or adenovirus and other known non-retroviral promoters capable of controlling gene expression.

Useful expression vectors, for example, may consist of segments of chromosomal, non-chromosomal and synthetic DNA sequences, such as various known derivatives of SV40 and known bacterial plasmids, e.g., pUC, pBlueScript™ plasmids from $E.\ coli$ including pBR322, pCR1, pMB9, pUC, pBlueScript™ and their derivatives.

Expression vectors containing the geneticin (G418) or hygromycin drug selection genes (Southern, P. J., $In\ Vitro$, 18, p. 315 (1981), Southern, P. Jet al., $J.\ Mol.\ Appl.\ Genet.$, 1, p. 327 (1982)) are also useful. These vectors can employ a variety of different enhancer/promoter regions to drive the expression of both a biologic gene of interest (e.g., NGF) and/or a gene conferring resistance to selection with toxin such as G418 or hygromycin B. The G418 resistance gene codes for aminoglycoside phosphotransferase (APH) which enzymatically inactivates G418 (100–500 g/l) added to the culture medium. Only those cells expressing the APH gene will survive drug selection usually resulting in the expression of the second biologic gene as well. The hygromycin B phosphotransferase (HBH) gene codes for an enzyme which specifically modifies hygromycin toxin and inactivates it. Genes cotransfected with or contained on the same plasmid as the hygromycin B phosphotransferase gene will be preferentially expressed in the presence of hygromycin B at 50–200 g/ml concentrations.

A variety of different mammalian promoters can be employed to direct the expression of the genes for G418 and hygromycin B and/or the biologic gene of interest. Examples of expression vectors that can be employed are the commercially available pRC/CMV, pRC/RSV, and pCDNA1NEO (InVitrogen).

In one embodiment, the pNUT expression vector is used. Baetge et al., $PNAS$, 83, pp. 5454–58 (1986). In addition, the pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

In a preferred embodiment, we contemplate insertion of the human Epo CDNA into high expression vectors containing housekeeping gene promoter such as CMV (Cytomegalovirus), PGK-1 (Phospho-glycerate kinase-1), or MT-1 (Metalothionein). We most prefer the PGK-1 promoter. The sequence of the PGK-1 promoter is known. Adra et al., *Gene*, 60, pp. 65–74 (1987).

Regulation of expression may be achieved using hypoxia-sensitive regulatory elements. Previous studies have shown that promoter and enhancer elements in the 5' and 3' flanking region of the human erythropoietin gene could promote the increase of the EPO production under hypoxic conditions. The human EPO hypoxia inducible enhancer region comprises a tripartite structure which begins 115 nucleotides 3' to the EPO adenylation site. Beck et al., *J Biol Chem* 266(24): 15563 (1991); Beck et al., *Blood* 82(3): 70 (1993); Blanchard KL et al., *Mol Cell Biol* 12(12): 5373 (1992); Goldberg MA et al., *Proc Natl Acad Sci USA* 84: 7972 (1987); Madan A et al., *Proc Natl Acad Sci USA* 90: 3928 (1993).

Alternatively, other suitable hypoxia responsive elements may be used to generate an EPO-producing cell in which the production of EPO is regulated. In a preferred embodiment we contemplate use of cells transfected with at least one hypoxia responsive element from the 5' flanking sequence of the phosphoglycerate kinase I gene. The PGK-1 hypoxia responsive element is an 18 mer element within the PGK-1 promoter sequence, and has the following sequence:

5' GTCGTGCAGGACGTGACA 3' (SEQ ID NO:1)

This element has sequence and protein binding similarities to the hypoxia inducible factor 1 binding domain within the EPO 3' enhancer.

Insertion of more than one copy of this PGK-derived 18 mer is contemplated to provide greater hypoxia responsiveness. Preferably between two to ten copies are inserted 5' to the PGK promoter (or other suitable promoter) in the transfected cells. In a specific embodiment we contemplate insertion of a tandem repeat of the 18 mer, having the following sequence:

5' GTCGTGCAGGACGTGACA CTCGC GTCGTG-CAGGACGTGACA 3' (SEQ ID NO:2)

Both allogeneic and xenogeneic cells may be used. Use of a cell line of xenogeneic origin provides an additional advantage since the transplanted cells will be rejected by the host immune system in the event of device breakage.

These cells are surrounded with a permselective membrane which permits the diffusion of small molecules such as nutrients and trophic factors into and out of the polymer envelope, while excluding larger molecules of the immune system (antibodies, complement, etc.).

A wide variety of cells may be used. These include well known, publicly available immortalized cell lines as well as dividing primary cell cultures. Examples of suitable publicly available cell lines include, chinese hamster ovary (CHO), mouse fibroblast (L-M), NIH Swiss mouse embryo (NIH/3T3), African green monkey cell lines (including COS-1, COS-7, BSC-1, BSC-40, BMT-10 and Vero), rat adrenal pheochromocytoma (PC12 and PC12A), AT3, rat glial tumor (C6), astrocytes and other fibroblast cell lines. Primary cells that may be used include, EGF-responsive neurospheres, bFGF-responsive neural progenitor stem cells derived from the CNS of mammals (Richards et al., *PNAS* 89, pp. 8591–8595 (1992); Ray et al., *PNAS* 90, pp. 3602–3606 (1993)), primary fibroblasts, Schwann cells, astrocytes, β-TC cells, Hep-G2 cells, oligodendrocytes and their precursors, myoblasts (including $C_2C_{12}$ cells) and the like.

Cell lines offer several advantages including unlimited availability, the possibility of rapid screening in vitro for the presence of pathogens from which cell banks are established, and the suitability for stable gene transfer using non-viral-based recombinant DNA techniques. One preferred cell line chosen for the gene transfer technique are baby hamster kidney (BHK) cells. Other preferred cell lines are myoblasts, including C2C12 cells, most preferably C2C12 cells.

A particular advantage to using xenogeneic over allogeneic cells is that in the unlikely event of membrane failure, the xenogeneic cells are more likely to be targeted for destruction by the immune system when compared to allogeneic cells. Furthermore, xenogeneic sources are easy to obtain and their use precludes the necessity for the use of human tissue which is difficult to obtain and fraught with societal and ethical considerations. In addition, human tissue may contain adventitious agents that are more readily transmitted to the transplantation recipient. Finally, use of xenogeneic tissue and cell lines for transplantation in humans removes the risks associated with the handling and processing of human tissue.

Increased expression can be achieved by increasing or amplifying the copy number of the transgene encoding EPO or other suitable biologically active molecule(s), using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841).

EPO levels may be monitored either by ELISA or by bioassay (Naffakh et al., *Proc. Natl. Acad. Sci. USA*, 92, pp. 3194–98 (1995).

The methods of this invention may be used in combination with other therapies. Likewise, other molecules may be co-delivered to the patient, e.g., immunosuppresive molecules such as CR-1.

Co-delivery can be accomplished in a number of ways. Cells may be transfected with separate constructs containing the genes encoding the described molecules. Alternatively, cells may be transfected with a single construct containing two or more genes.

Multiple gene expression from a single transcript is preferred over expression from multiple transcription units. One approach for achieving expression of multiple genes from a single eukaryotic transcript takes advantage of sequences in picorna viral mRNAs known as internal ribosome entry sites ("IRES"). These sites function to facilitate protein translation from sequences located downstream from the first AUG of the mRNA.

Macejak and Sarnow reported that the 5' untranslated sequence of the immunoglobulin heavy chain binding protein (BiP, also known as CRP 78, the glucose-regulated protein of molecular weight 78,000) mRNA can directly confer internal ribosome binding to an mRNA in mammalian cells, in a 5'-cap independent manner, indicating that translation initiation by an internal ribosome binding mechanism is used by this-cellular mRNA. Macejak, *Nature*, 353, pp. 90–94 (1991).

WO 94/24870 refers to use of more than two IRES for translation initiation from a single transcript, as well as to use of multiple copies of the same IRES in a single construct.

Various modified IRES sequences are known. See, e.g., Mountford and Smith, *Trends Genet.*, 11, pp. 179–84 (1995); Dirks et al., *Gene*, 128, pp. 247–49 (1993); Martinez-Salas et al., *J. Virology*, 67, pp. 3748–55 (1993) and Mountford et al., *Proc. Nati. Acad. Sci. USA*, 91, pp. 4303–07 (1994). Use of these modified sequences is also contemplated in this invention.

Also contemplated is encapsulation of two or more separately transfected cells or cell lines, each secreting one of the desired molecules.

This invention also contemplates use of different cell types during the course of the treatment regime. For example, a patient may be implanted with a capsule device containing a first cell type (e.g., hEPO-secreting BHK cells). If after time, the patient develops an immune response to that cell type, the capsule can be retrieved, or explanted, and a second capsule can be implanted containing a second cell type (e.g., $C_2C_{12}$ cells). In this manner, continuous provision of the therapeutic molecule is possible, even if the patient develops an immune response to one of the encapsulated cell types.

Encapsulation hinders elements of the immune system from entering the capsule, thereby protecting the encapsulated cells from immune destruction. This technology increases the diversity of cell types that can be employed in therapy. The semipermeable nature of the capsule membrane also permits the molecule of interest to easily diffuse from the capsule into the surrounding host tissue. This technique prevents the inherent risk of tumor formation and allows the use of unmatched human or even animal tissue, without immunosuppression of the recipient. Moreover, the implant may be retrieved if necessary or desired. It is both undesirable and expensive to maintain a patient in an immunosuppressed state for a substantial period of time. Such retrievability may be essential in many clinical situations.

Numerous encapsulation devices are-known, having various outer surface morphologies and other mechanical and structural characteristics. Capsules have been categorized as Type 1 (T1), Type 2 (T2), type ½ (T½) or Type 4 (T4) depending on their outer surface morphology. Such membranes are described, e.g., in Lacy et al., *Science*, 254, pp. 1782–84 (1991), Dionne et al., PCT/US92/03327 and Baetge, WO 95/05452.

As used herein "a biocompatible capsule" means that the capsule, upon implantation in a host mammal, does not elicit a detrimental host response sufficient to result in the rejection of the capsule or to render it inoperable, for example through degradation.

As used herein "an immunoisolatory capsule" means that the capsule upon implantation into a mammalian host minimizes the deleterious effects of the host's immune system on the cells within its core.

A variety of biocompatible immunoisolatory capsules are suitable for delivery of molecules according to this invention. Such capsules will allow for the passage of metabolites, nutrients and therapeutic substances while minimizing the detrimental effects of the host immune system. Preferably the capsule of this invention will be similar to those described in Aebischer et al., PCT publication WO 92/19195, incorporated herein by reference.

Useful biocompatible polymer capsules comprise (a) a core which contains a cell or cells, either suspended in a liquid medium or immobilized within a hydrogel or extracellular matrix components (or other suitable molecules), and (b) a surrounding or peripheral region of permselective matrix or membrane (jacket) which does not contain isolated cells, which is biocompatible, and which is sufficient to protect isolated cells if present in the core from detrimental immunological attack.

The core of the polymer capsule is constructed to provide a suitable local environment for the continued viability and function of the cells isolated therein.

Many transformed cells or cell lines are most advantageously isolated within a capsule having a liquid core. For example, cells can be isolated within a capsule whose core comprises a nutrient medium, optionally containing a liquid source of additional factors to sustain cell viability and function, such as fetal bovine or equine serum.

Suitably, the core may be composed of a matrix formed by a hydrogel which stabilizes the position of the cells in cell clumps. The term "hydrogel" herein refers to a three dimensional network of cross-linked hydrophilic polymers. The network is in the form of a gel, substantially composed of water, preferably but not limited to gels being greater than 90% water.

Compositions which form hydrogels fall into three classes. The first class carries a net negative charge (e.g., alginate). The second class carries a net positive charge (e.g., collagen and laminin). Examples of commercially available extracellular matrix components include Matrigel™ and Vitrogen™. Fibroblasts generally survive well in a positively charged matrix and are thus suitably enclosed in extracellular-matrix type hydrogels. The third class is net neutral in charge (e.g., highly crosslinked polyethylene oxide, or polyvinylalcohol). Any suitable matrix or spacer may be employed within the core, including precipitated chitosan, synthetic polymers and polymer blends, microcarriers and the like, depending upon the growth characteristics of the cells to be encapsulated.

Preferably, the capsules are immunoisolatory. To be immunoisolatory, the surrounding or peripheral region of the capsule should confer protection of the cells from the immune system of the host in whom the capsule is implanted, by preventing harmful substances of the host's body from entering the core of the vehicle, and by providing a physical barrier sufficient to prevent detrimental immunological contact between the isolated cells and the host's immune system. The thickness of this physical barrier can vary, but it will always be sufficiently thick to prevent direct contact between the cells and/or substances on either side of the barrier. The thickness of thisregion generally ranges between 5 and 200 microns; thicknesses of 10 to 100 microns are preferred, and thickness of 20 to 75 microns are particularly preferred. Types of immunological attack which can be prev,ented or minimized by the use of the instant vehicle include attack by macrophages, neutrophils, cellular immune responses (e.g. natural killer cells and antibody-dependent T cell-mediated cytolysis (ADCC), and humoral response (e.g., antibody-dependent, complement-mediated cytolysis).

Use of immunoisolatory capsules allows the implantation of xenogeneic cells or tissue, without a concomitant need to immunosuppress the recipient. Use of immunoisolatory capsules also allows use of unmatched cells (allografts). The type and vigor of an immune response to xenogeneic cells is expected to differ from the response encountered when syngeneic or allogeneic tissue is implanted into a recipient. This response may proceed primarily by cell-mediated, or by complement-mediated attack; the determining parameters in a particular case may be poorly understood. However, the exclusion of IgG from the core of the vehicle is not the touchstone of immunoprotection, because in most cases IgG alone is insufficient to produce cytolysis of the target cells or tissues. Using immunoisolatory macrocapsules, it is possible to deliver needed high molecular weight products or to provide metabolic functions pertaining to high molecular weight substances, provided that critical substances necessary to the mediation of immunological attack are excluded from the immunoisolatory capsule. These substances may comprise the complement attack complex component Clq, or they may comprise phagocytic or cytotoxic cells; the instant immunoisolatory capsule provides a protective barrier between these harmful substances and the isolated cells. Thus, an immunoisolatory capsule can be used for the delivery even from xenogeneic cells, products having a wide range of molecular sizes. Accordingly, for immnunoisolatory capsules nominal molecular weight cutoff (MWCO) values between 50–2000 kD are contemplated. Preferably, the MWCO is between 50–700 kD. Most preferably, the MWCO is between 70–300 kD.

Various polymers and polymer blends can be used to manufacture the capsule jacket, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted configurations which tend to lead to migration of the capsules from the site of implantation, such as spherical capsules small enough to travel in the recipient's blood vessels, are not preferred. Certain shapes, such as rectangles, patches, disks, cylinders, and flat sheets offer greater structural integrity and are preferable where retrieval is desired.

In one embodiment, the implantable capsule is of a sufficient size and durability for complete retrieval after implantation. Preferably the device has a tether that aids in retrieval. Such tethers are well known in the art. Such macrocapsules have a core of a preferable minimum volume of about 1 to 10 $\mu$l and depending upon use are easily fabricated to have a volume in excess of 100 $\mu$l.

In one embodiment the capsule will have an inner single ultrafiltration membrane with a permselective pore-size permeability range of 60–98% BSA rejection coefficient and 50–90% ovalbumin rejection coefficient.

In a hollow fiber configuration, the fiber all typically have an inside diameter of less than 1500 microns, preferably less than 300–600 microns. In either geometry, the hydraulic permeability will typically be in the range of 1–100 mls/min/$M^2$/mmHg, preferably in the range of 25 to 70 mls/min/$M^2$/mmHg. The glucose mass transfer coefficient of the capsule, defined, measured and calculated as described by Dionne et al., *ASAIO Abstracts*, p. 99 (1993), and Colton et al., *The Kidney*, eds., Brenner BM and Rector FC, pp. 2425–89 (1981) will be typically greater than $10^{-6}$ cm/sec, preferably greater than $10^{-4}$ cm/sec.

T1 membranes may be formed by coextrusion of a polymer solution and coagulant solution through air before entering a quench bath. T2 membranes may be formed by coextruding the polymer, and coagulation solutions into humidified air or a mist and then into a bath. T4 membranes may be formed by coextrusion of the polymer and coagulant solutions directly into a coagulant bath, so that formation of the permselective membrane occurs on both outer and inner wall surfaces simultaneously. Methods of making biocompatible, immunoisolatory semipermeable hollow fiber membranes are disclosed in U.S. Pat. No. 5,284,761 and 5,158,881, herein incorporated by reference.

T½ membranes may be formed using similar methods used to form T2 membranes. However, the mist or humidity at the coextrusion port may be controlled according to known methods to produce the desired outer surface morphology. Alternatively, the nozzle distance from a quench bath may be varied, according to routine methods. Further, if coextrusion is used to cast the membrane, the absolute and/or relative flow rates of polymer and coagulant may be adjusted to achieve the desired outer wall surface morphology. Finally, the polymer and coagulant solution compositions and temperatures can be varied to achieve the desired outer surface wall morphology. See WO 95/0542.

Any suitable method of sealing the capsules may be used, including the employment of polymer adhesives and/or crimping, knotting and heat sealing. These sealing techniques are known in the art. In addition, any suitable "dry" sealing method can also be used. In such methods, a substantially non-porous fitting is provided through which the cell-containing solution is introduced. Subsequent to filling, the capsule is sealed. Such a method is described in copending U.S. application Ser. No. 08/082,407, herein incorporated by reference.

In a preferred embodiment, the capsule is formed from a polyether sulfone hollow fiber, such as those described in U.S. Pat. Nos. 4,976,859 and 4,968,733, herein incorporated by reference. Such capsules jackets may be permselective, or may be microporous. In other embodiments we contemplate using microcapsules for cellular delivery. See, e.g., U.S. Pat. No. 4,352,883; 4,353,888, and 5,084,350, herein incorporated by reference. Likewise, we also contemplate polymer rods (e.g., EVA rods) for delivery of EPO.

The methods and devices of this invention are intended for use in a mammalian host, recipient, patient, subject or individual, preferably a primate, most preferably a human.

A number of different implantation sites are contemplated for the devices and methods of this invention. These implantation sites include subcutaneous, intravenous, intramuscular, preferably subcutaneous.

The actual dosage can be varied by any suitable method known in the art, including, e.g., by implanting a fewer or greater number of capsules. If the cells are encapsulated in macrocapsules, we prefer implanting between one and ten capsules. The dosage should be sufficient to produce a therapeutic effect. The cell loading density may also be varied over a wide range. If macrocapsules are used, typically between $10^3$ and $10^8$ cells are encapsulated per capsule, preferably $10^5$ to $10^7$ cells are encapsulated, most preferably about $10^6$ cells.

The cells, methods and devices of this invention may be useful in the treatment of human hemoglobinopathies. The clinical applications of EPO are rapidly expanding. Lifelong treatment with very high doses is now under evaluation for hemoglobinopathies. Rodgers GP et al., *New England Journal of Medicine* 328: 73 (1993). In particular, the devices and methods of this invention may be used in the treatment of disease states associated with deficient levels of EPO.

Deficient levels of EPO production have been associated with numerous forms of anemia, including anemia resulting from renal failure and end-stage renal disease, anemias of chronic infection, auto-immune diseases, anemia of prematurity, anemia of hypothyroidism, and anemia of malnutrition.

For renal insufficiency, approximately 3000 to 10000 UI/week is currently administered by subcutaneous injection. For B-thalassemia, approximately 150,000 UI/day are administered. Using the devices and methods of this invention, delivery of such therapeutically effective amounts of EPO can routinely be achieved. Further, continuous capsular delivery may permit lowering the dosage requirement due to higher bioavailability of the cell-produced EPO.

In one embodiment of this invention, we provide hypoxia responsive cells that produce up to between 644–750 UI EPO/$10^6$ cells/day (produced under normoxic conditions). At about this level of production, to deliver between 3000–10,000 UI/week, a single macrocapsule containing about $10^6$ cells would be sufficient to deliver a therapeutic dosage. Likewise, to deliver up to 150,000 UI/day, e.g., two devices each containing about $10^8$ cells would be sufficient. And, as noted above, a lower dosage may be required using the devices and methods of this invention, rather than traditional delivery methods.

Animal models are available for pre-clinical assessment. A mouse model of beta-thalassemia caused by the deletion of the mouse beta-major globin gene has been described. Skow LC et al., *Cell* 34: 1043 (1983). That model has been shown to be a reasonable model for studying specific therapies for human beta-thalassemia. Leroy-Viard K et al., *Blood* 78(6): 1596 (1991); Villeval J-L et al., *Blood* 84(3): 928 (1994). In these mice, repeated injections of EPO increase expression of the B-minor globin, as well as the hemoglobin level, and improve the erythrocyte phenotype of beta-thalassemic mice—i.e., it reduces the amount of unpaired and insoluble a-hemoglobin chains and the membrane protein defects, which characterize both murine and human beta-thalassemic erythrocytes.

Brunner et al., *Kidney International* 36: 969 (1989); Brunner FP, *Clinical Nephrology* 25: 148 (1986) refer to a second model. They reported pharmacological studies in Wistar rats with markedly reduced renal mass. Typically, the left renal pedicle of the rats is carefully dissected through a midline abdominal incision. Then two or three upper branches of the left renal artery is tied off. One week later, the right kidney is removed after ligating the right renal pedicle from a flank incision. After few weeks, the rats are placed in metabolic cages.

Finally, a large animal model (normal and uremic sheep) has also been described. Eschbach JW et al., *Kidney International* 18: 72 (1980); Mladenovic J et al., *J Lab Clin Med* 105(6): 65 (1980); Widness JA et al., *Journal of Pharmacology and Experimental Therapeutics* 261(3): 977 (1992); Eschbach JW et al., *J Clin Invest* 74: 434 (1984). A model of chronic renal failure was created by two-stage, subtotal nephrectomy. Sheep are maintained in hemodialysis and stable uremia is created. The sheep is a good model because of two advantages: (1) vascular access can be maintained for a prolonged period of time free of infection, and (2) by selecting animals for hemoglobin phenotype, it is possible to take advantage of an unusual hematopoietic property of certain ruminants, the appearance of a structurally distinct hemoglobin, hemoglobin C, in response to erythropoietin stimulation.

EXAMPLES

Example 1

Construction of C2C12/EPO Cell Line

We constructed a C2C12 cell line secreting rhEPO. The cell line was tested in various in vitro and in vivo models.

Plasmid construction

The plasmid pCI-Neo was purchased from Promega Corporation (Madison, Wis., USA). This plasmid was modified as follows. A mutated dihydrofolate reductase gene (DHFR) under the control of the SV40 promoter as well as the Hepatitis virus B 3' untranslated region (HBV-3' UTR) were isolated from a modified pNUT vector (Baetge et al, *Proc. Natl. Acad. sci. USA*, 83, pp. 5454–58 (1986) digested with PvuII. The isolated fragment was subcloned into the pCI-Neo vector digested by BamHI and blunted by filling in the protruding ends with T4 polymerase resulting in pCI-Neo-DHFR plasmid.

The mouse phosphoglycerate kinase 1 (PGK-1) promoter was exised from pCI-PGK-GIP-R/IRES/GLP-1-R vector (kindly provided by B. Thorens, Lausanne, Switzerland) by BglII/EcoRI digestion and cloned into the BglII/Eco RI isolated pCI-Neo-DHFR backbone giving rise to pPI-Neo-DHFR vector.

The mouse MT-1 promoter was removed from a modified pNUT vector (Baetge et al., supra) by PCR, then digested with BglII/PvuII and cloned into the BglII/EcoRI isolated pCI-Neo backbone resulting in the pMI-Neo vector. The mutated dihydrofolate reductase gene (DHFR) under the control of the SV40 promoter as well as the Hepatitis virus B 3' untranslated region (HBV-3' UTR) were isolated from the RP3224D plasmid digested with BamHI and cloned into BamHI digested pMI-Neo vector resulting in pMI-neo-DHFR vector.

Figure 2:
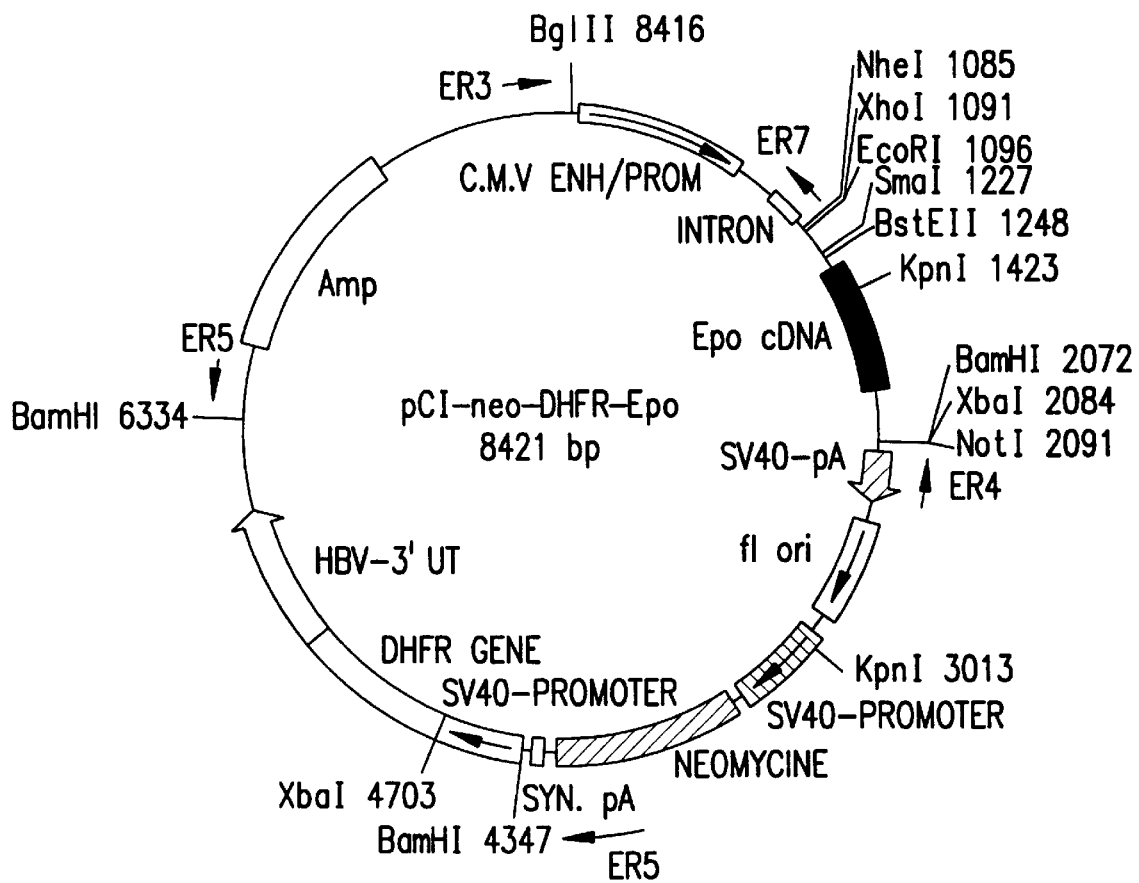
FIG. 2: Plasmid map of pCI-neo-DHFR-EPO vector containing the human EPO gene. Features of the vector include cytomegalovirus immediate-early enhancer (bp 1–659); cytomegalovirus immediate-early promoter (bp 669–750); chimeric intron (bp 890–1022); T7 promoter (bp 1067–1085); EPO cDNA (bp 1379–1879); T3 promoter (bp 2097–2118); SV40 late polyadenylation signal (bp 2127–2348); phage f1 region (bp 2443–2898); SV40 enhancer and early promoter (bp 2962–3380); SV40 minimum origin of replication (bp 3278–3343); coding region of neomycin phosphotransferase (bp 3425–4219); synthetic polyadenylation signal (bp 4283–4331); SV40 promoter (bp 4352–4710); mutated DHFR gene Fnu4H1 (bp 4711–5361); HBV-3' UTR (bp 5362–5949); β-lactamase coding region (bp 6729–7589).

The plasmid pBluescript II SK+ (Stratagene, Calif., USA) containing the cDNA for human erythropoietin, kindly provided by Dr. Y. Beuzard (Laboratory of Experimental Gene Therapy, Paris, France), was digested by EcoRI/NotI. The isolated fragment was then cloned into the three above described vectors. The integrity of the final constructs pCI-neo-DHFR-Epo (map shown in FIG. 2), pMI-neo-DHFR-Epo and pPI-neo-DHFR-Epo (map shown in FIG. 1) was confirmed by restriction analysis and sequencing.

Cell culture and transfection of $C_2C_{12}$ cells

Mouse $C_2C_{12}$ myoblasts derived from leg skeletal muscle of an adult C3H mouse were obtained from American Type Culture Collection (ATCC; CRL 1777, Rockville, Md.). $C_2C_{12}$ cells were grown in Dulbecco's modified Eagle's medium (DMEM) containing 10% fetal calf serum (FCS), 2mM L-glutamine, 4.5 g/l glucose, 100U/ml penicillin, 100U/ml streptomycin. The cells were transfected by calcium phosphate precipitation (Mammalian transfection kit, Stratagene) with plasmids pCI-neo-DHFR-Epo, pMI-neo-DHFR-Epo and pPI-neo-DHFR-Epo.

After 2 wveeks of incubation with 0.8 mg/ml G418 cells were incubated with increasing concentrations of methotrexate (1–200 gM) over a 6 weeks period thus amplifying the number of copies of integrated plasmids. Stability of transgene expression was achieved by 6 alternating weeks of cell incubation with either 0.8 mg/ml G418 or 200 μM MTX. Clones were obtained by limiting dilution.

Measurement of medium rhEPO concentrations $C_2C_{12}$ cells were plated in growth medium at density of $1\times10^5$ cells per well in 6-well culture dishes (Costar). Differentiated encapsulated cells were placed in PC-1 medium, a serum free medium containing human recombinant protein (Hycor Biomedical Inc., Calif.). Conditioned media were obtained by incubating the $C_2C_{12}$ cells encapsulated or not in 1 ml of fresh medium for 1 hour. The samples were stored at –20° C. until determination of rhEPO concentrations using an enzyme linked immunosorbent assay (ELISA) system (Quantikine IVD, R&D Systems, Minneapolis, Minn.).

Transfected cells were assayed for EPO production. Cells transfected with pCI-neo-DHFR-Epo produced (average secretion of pool) 10 UI/$10^6$ cells/day. Cells transfected with pMI-neo-DHFR-Epo produced (average secretion of pool) 60 UI/$10^6$ cells/day. Finally, pooled cells (or clones isolated by limiting dilution) transfected with pPI-neo-DHFR-Epo produced EPO as reported in the Table below.

| huEpo secretion of pPI-neo-DHFR-huEpo-transfected $C_2C_{12}$ cells | | |
|---|---|---|
| Pool | 150 IU/$10^6$ cells/24h | 1.2μg/$10^6$ cells/24h |
| Pool/10 #5 | 305 IU/$10^6$ cells/24h | 2.3μg/$10^6$ cells/24h |
| Pool/10 #6 | 354 IU/$10^6$ cells/24h | 2.7μg/$10^6$ cells/24h |
| Pool/10 #10 | 436 IU/$10^6$ cells/24h | 3.4μg/$10^6$ cells/24h |
| Clone #1 | 373 IU/$10^6$ cells/24h | 2.9μg/$10^6$ cells/24h |
| Clone #2 | 750 IU/$10^6$ cells/24h | 5.8μg/$10^6$ cells/24h |
| Clone #3 | 644 IU/$10^6$ cells/24h | 5.0μg/$10^6$ cells/24h |
| Clone #5 | 111 IU/$10^6$ cells/24h | 0.9μg/$10^6$ cells/24h |
| Clone #6 | 199 IU/$10^6$ cells/24h | 1.5μg/$10^6$ cells/24h |
| Clone #7 | 640 IU/$10^6$ cells/24h | 4.9μg/$10^6$ cells/24h |
| Clone #8 | 458 IU/$10^6$ cells/24h | 3.5μg/$10^6$ cells/24h |
| Clone #9 | 417 IU/$10^6$ cells/24h | 3.2μg/$10^6$ cells/24h |
| Clone #10 | 339 IU/$10^6$ cells/24h | 2.6μg/$10^6$ cells/24h |
| Clone #11 | 318 IU/$10^6$ cells/24h | 2.4μg/$10^6$ cells/24h |
| Clone #13 | 446 IU/$10^6$ cells/24h | 3.4μg/$10^6$ cells/24h |
| Clone #14 | 423 IU/$10^6$ cells/24h | 3.2μg/$10^6$ cells/24h |

After freezing, clone 3 produced about 4 μg/$10^6$ cells/day.

Figure 3:
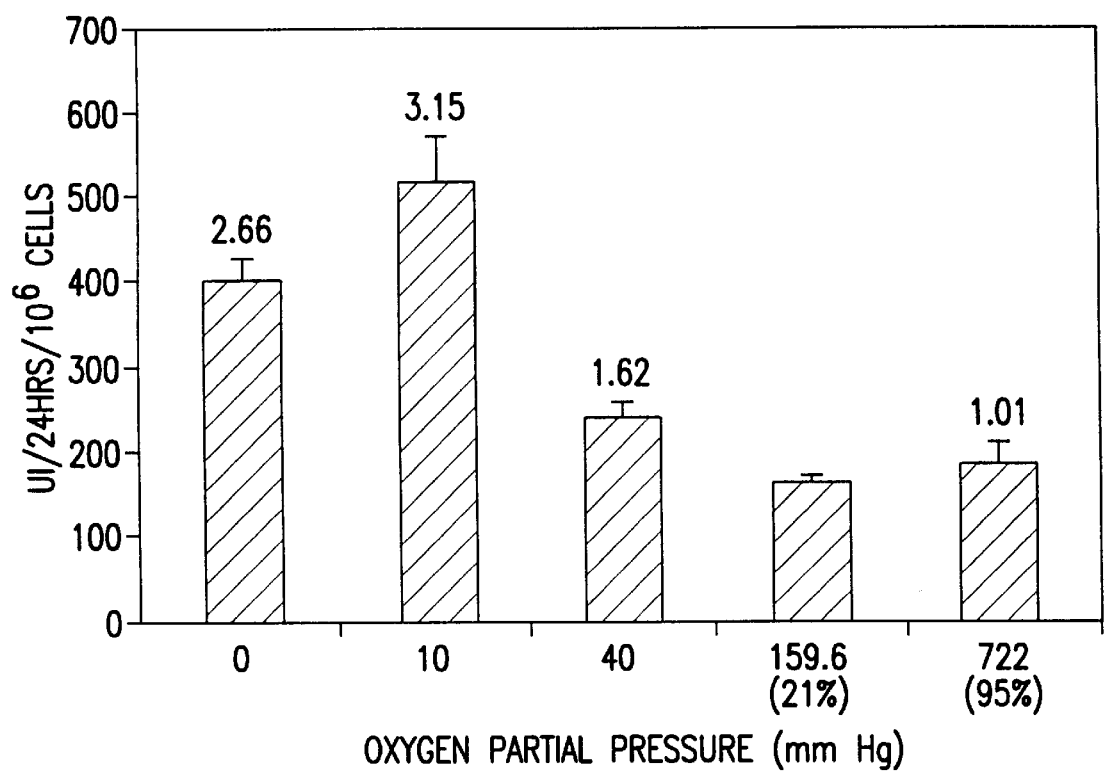
FIG. 3: In vitro production of EPO by engineered myoblasts under various oxygen concentrations. EPO secretion is expressed in UI/$10^6$ cells/day.

After removal of drug selection for one month, no significant difference was detected in expression of rhEPO in transfected cells (data not shown), confirming the stability of transgene expression in myoblasts. The functional activity of the produced EPO was confirmed by incubation of culture supernatants with EPO-dependent murine cell line DaE7.

pPI-neo-DHFR-huEpo-transfected cells from pool/10 above (producing about 150 IU/$10^6$ cells/24 h) were evaluated for hypoxia responsiveness. Unencapsulated cells were were cultured in Petri dishes on a thin film that is permeable to $O_2$ (Petriperm). The Petri dishes were exposed to a constant stream of $O_2$ at concentrations of 0, 10, 40, 159.6 (normoxic) or 722 mm Hg oxygen. As the data in FIG. 3 shows, there was hypoxic induction of EPO production— under 10 mm Hg oxygen, this induction was 3-fold the normoxic level or EPO production.

Example 2

Cell Encapsulation

Control and transfected $C_2C_{12}$ cells were harvested and diluted in order to obtain a final cell suspension of $1 \times 10^5$ cells/μl. For experiments in which a matrix was used in the capsule core, the final cell density was 100,000 cells/gl in 1.75 mg/ml Zyderm (Collagene S. A., Lausanne, Switzerland). For experiments where no matrix was used, I.e., a liquid core in the capsule, the final cell suspension was also 100,000 cells/μl.

The cell suspension was then injected into microporous polyethersulfone hollow fibers (OD: 550 μm, ID:350 μm) (Akzo Nobel Faser AG, Wupperthal, Germany). These fibers are described in U.S. Pat. No. 4,976,859 and 4,968,733, herein incorporated by reference.

One centimeter long capsules were made by cutting them to appropriate lengths and heat sealing the ends. Each capsule contains approximately $2 \times 10^5$ cells at the time of encapsulation. Capsules were placed during 3 days in DMEM medium containing 2% FCS at 37° C., 5% $CO_2$ for cell differentiation. Capsules were subsequently tested by ELISA assay and transfected in PC-1 medium for in vitro studies or implanted in mice for in vivo follow up biological effect.

Figure 4:
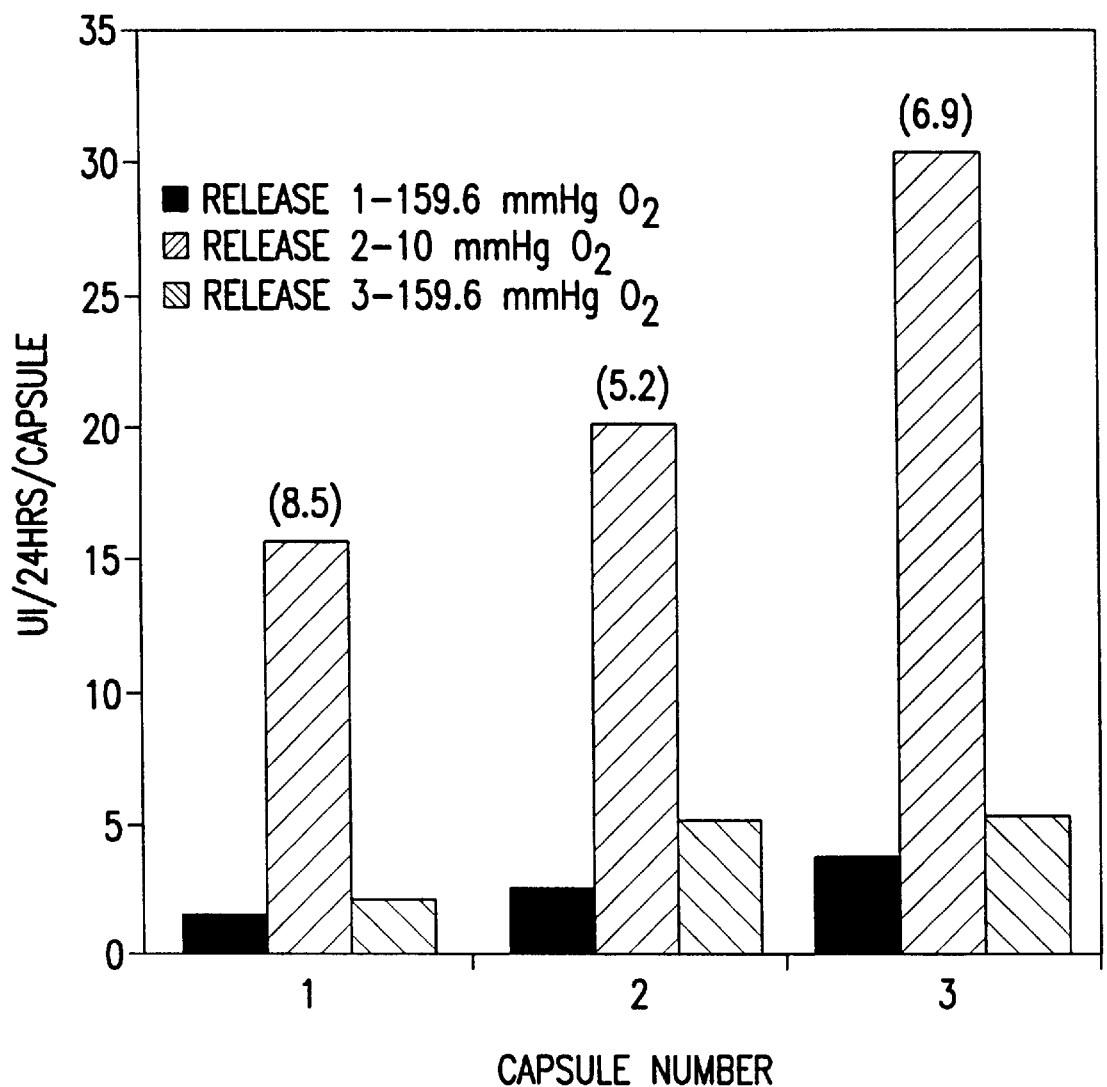
FIG. 4: In vitro production of EPO by encapsulated engineered myoblasts. Three capsules were exposed to a regime of nornoxic conditions for 24 hours, hypoxic conditions for 24 hours, and then returned to normoxic conditions for 24 hours. EPO secretion is expressed in UI/$10^6$ cells/day.

The cells of Example 1, encapsulated with a matrix core as described above, were assayed in vitro for hypoxic induction of EPO release. The data is shown in FIG. 4. A total of three capsules was used in this experiment. Each capsule was exposed to normoxic oxygen conditions (159.6 mm Hg oxygen) for a period of 24 hours and EPO production measured (shown as release 1 in FIG. 4). The capsule was then exposed to hypoxic conditions (10 mm Hg oxygen) (159.6 mm Hg oxygen) for a period of 24 hours and EPO production measured (show as release 2 in FIG. 4). Finally, the capsule was then returned-to normoxic conditions (159.6 mm Hg oxygen) for a period of 24 hours and EPO production measured (shown as release 3 in FIG. 4). As the data in FIG. 4 demonstrate, there is a between 5–8.5 fold increase in EPO production under hypoxic conditions. Further, EPO production by the encapsulated cells return to the normoxic level after return to normoxic conditions.

Example 3

Subcutaneous capsule implantation in adult rats and mice

Adult female C57BL/6, DBA/2J and C3H mice obtained from Iffa Credo (Saint-German sur l'Abresle, France) were anesthesized by inhalation of methoxyflurane (Metofane). Animals were placed in a prone position for surgery. A subcutaneous dissection was performed with a vertical lumbar incision. Capsules were carefully placed at one or two sites under the cutaneous tissue. The incisions were closed with two layers resorbable sutures (Vicryl 6.0 ). Upon recovery, the mice were returned to the animal care facility where they had access to food and water ad libittum.

The procedure for implanting rats (Fisher adult males, about 220 grams) was substantially the same as described above, except that the animals were anesthesized using pentobarbitol.
Hematocrit measurement Under general anesthesia, blood was drawn every two weeks from the tail vein into heparinized capillary tubes. The hematocrit was the measured by the microhematocrit method.
Capsules histology Capsules kept in vitro and those retrieved from in vivo experiments were fixed in 4% paraformaldehyde with 1% glutaraldehyde for three hours and dehydrated under alcohol cycle in preparation for glycol-methacrylate embedding (Leica). The capsules were cut at 6 μm thickness and stained with cresyl violet and eosine.
Detection of antibodies anti-rhEPO in mice serum A specific immunoperoxydase procedure using the Vectastain ABC system (Vector) on nitrocellulose bands was developed. Serial dilutions of rhEPO (Eprex, Cilag Laboratories) from 100 ng to 1 ng were blotted on 0.45 μm nitrocellulose membranes. Non-specific binding sites were then blocked by incubating the bands with 5% milk in tris buffer saline (TBS) pH 7.6. Bands were covered overnight with 60 μm of mice sera or PBS for negative control. Biotinylated goat anti-mouse (IgG (H+L) (Vector) was incubated with the bands followed by addition of the preformed Avidin Biotinylated horseradish peroxidase macromolecular Complex (ABC) (Vector). Finally signal detection was achieved using the diaminobenzidine tetrahydrochloride (DAB) chromogen (Pierce) which draw brown spots on the bands. After each procedure step 3–5 washes in phosphate buffer saline (PBS) was performed.

Figure 5:
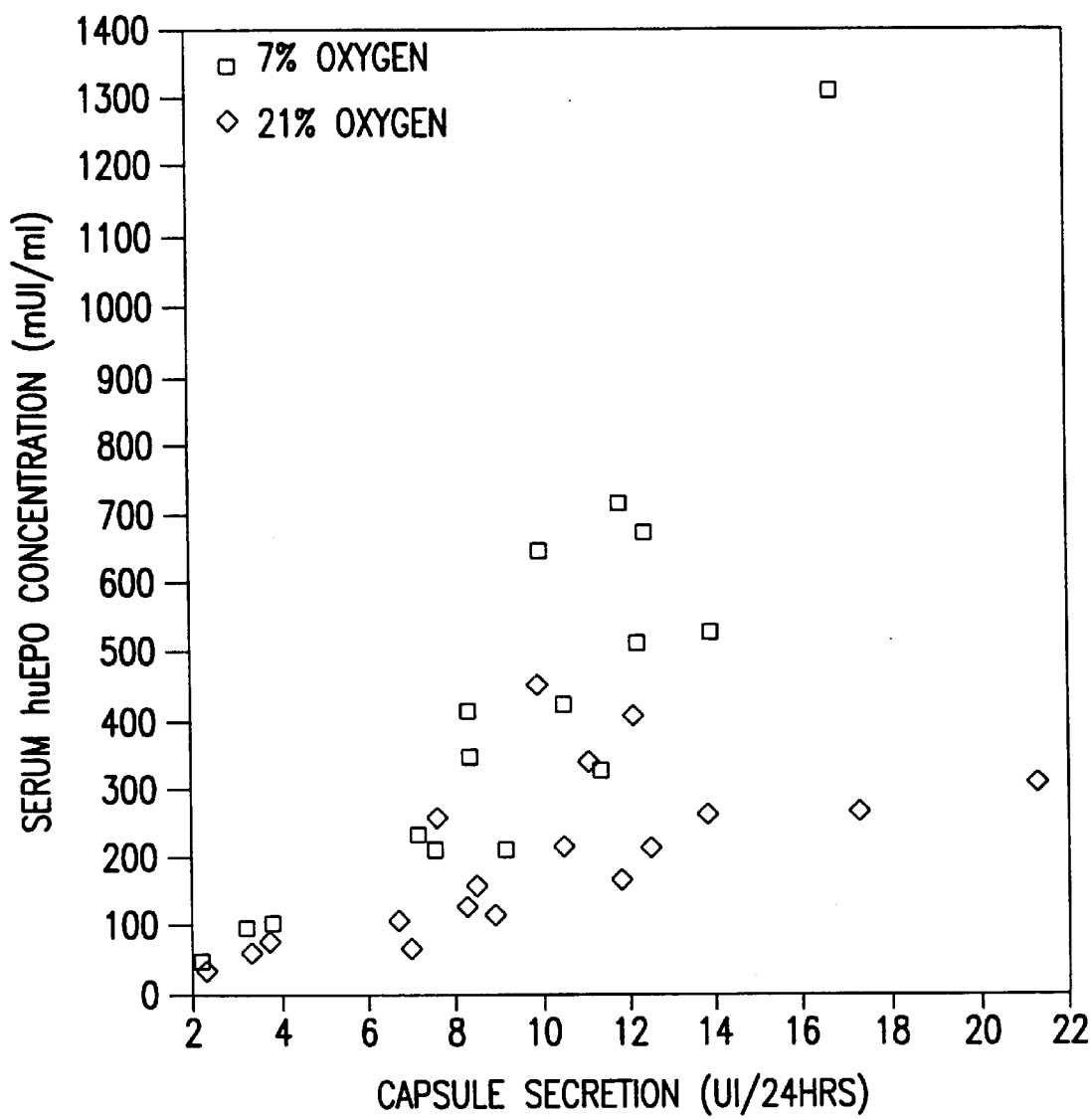
FIG. 5: In vivo regulation of EPO production by encapsulated engineered myoblasts in hypoxic mice. Mice were implanted with encapsulated EPO secreting cells and exposed to normoxic conditions or hypoxic conditions. The graph shows the correlation between capsule EPO secretion (UI/24 hours) and serum EPO concentration (mUI/ml).

We encapsulated the cells of Example 1 according to the encapsulation protocol of Example 2, and implanted capsules in mice as described above. In some capsules, the cells were immobilized in a matrix core, in others the cells were in a liquid core. Implanted mice were exposed to either a normoxic environment (21% oxygen) or hypoxic conditions (7% oxygen) for 24 hours. After this time, blood was taken from the animals for EPO assay. The data is shown in FIG. 5. Mouse serum EPO level is plotted as a function of capsular secretion of EPO. As the Figure shows, there is a strong correlation between capsular EPO release and serum EPO level.

In further experiments with mice implanted as described above, we monitored in vivo regulation of erythrpoietin production under nornoxic and hypoxic conditions, as reported in the following table:

| | In-Vivo Regulation of Encapsulated $C_2C_{12}$ Cells Expressing Human Erythropoietin | | | | |
|---|---|---|---|---|---|
| | Normoxia | | Hypoxia | | |
| Mouse | Capsule (UI/24hrs) | Serum (mUI/ml) | Capsule (UI/24hrs) | Serum (mUI/ml) | Induction |
| 1 | 3.3 | 56.8 | 3.2 | 95.8 | 1.69 |
| 2 | 7.0 | 72.4 | 7.1 | 230.8 | 3.19 |
| 3 | 2.3 | 33.0 | 2.2 | 43.1 | 1.31 |
| 4 | 3.7 | 74.3 | 3.8 | 100.8 | 1.36 |
| 5 | 6.7 | 105.9 | 7.5 | 210.4 | 1.99 |
| 6 | 8.9 | 113.5 | 9.1 | 211.8 | 1.87 |
| Average | 5.3 | 76 | 5.5 | 148.8 | 1.90 |

We encapsulated the cells of Example 1 according to the encapsulation protocol of Example 2, and implanted capsules in rats according to the protocol described above. A total of four rats were used in this study (two control; two treatment). The serum EPO level in each rat was assayed before capsule implantation.

Figure 6:
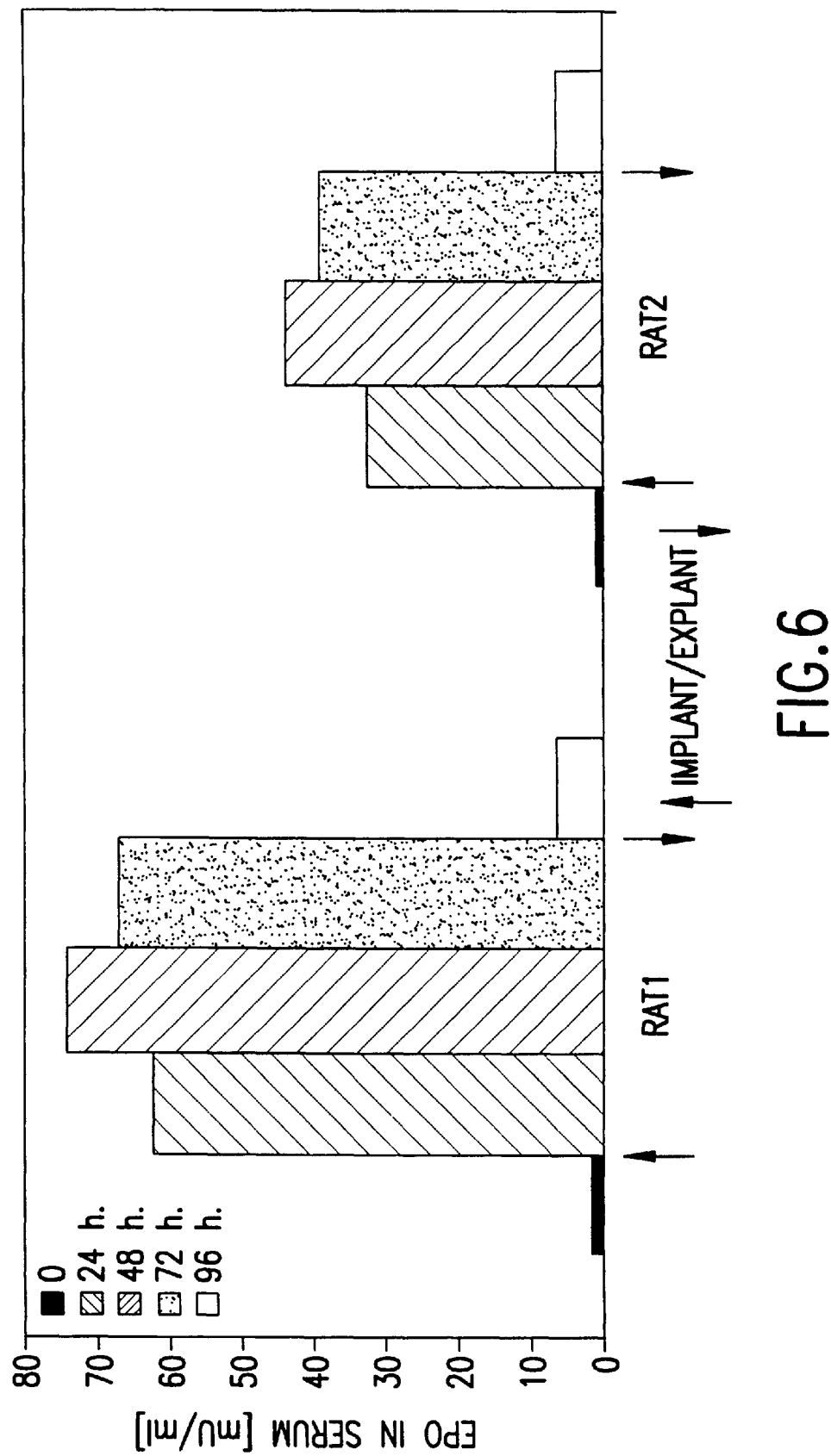
FIG. 6: In vivo regulation of human EPO production by encapsulated engineered myoblasts implanted into rats. The serum EPO levels (mUI/ml) are given two rats, over a 96 hour time frame, from prior to implant to post-explant. This figure shows the control experiment, in which the rats were exposed to normoxic oxygen conditions for the duration of the experiment.

The control rats were implanted with EPO producing capsules and exposed to normoxic conditions for 72 hours. The capsules were then explanted. As FIG. 6 shows, after implant, the serum EPO level rose, and then returned to its pre-implant level after the device was explanted.

Figure 7:
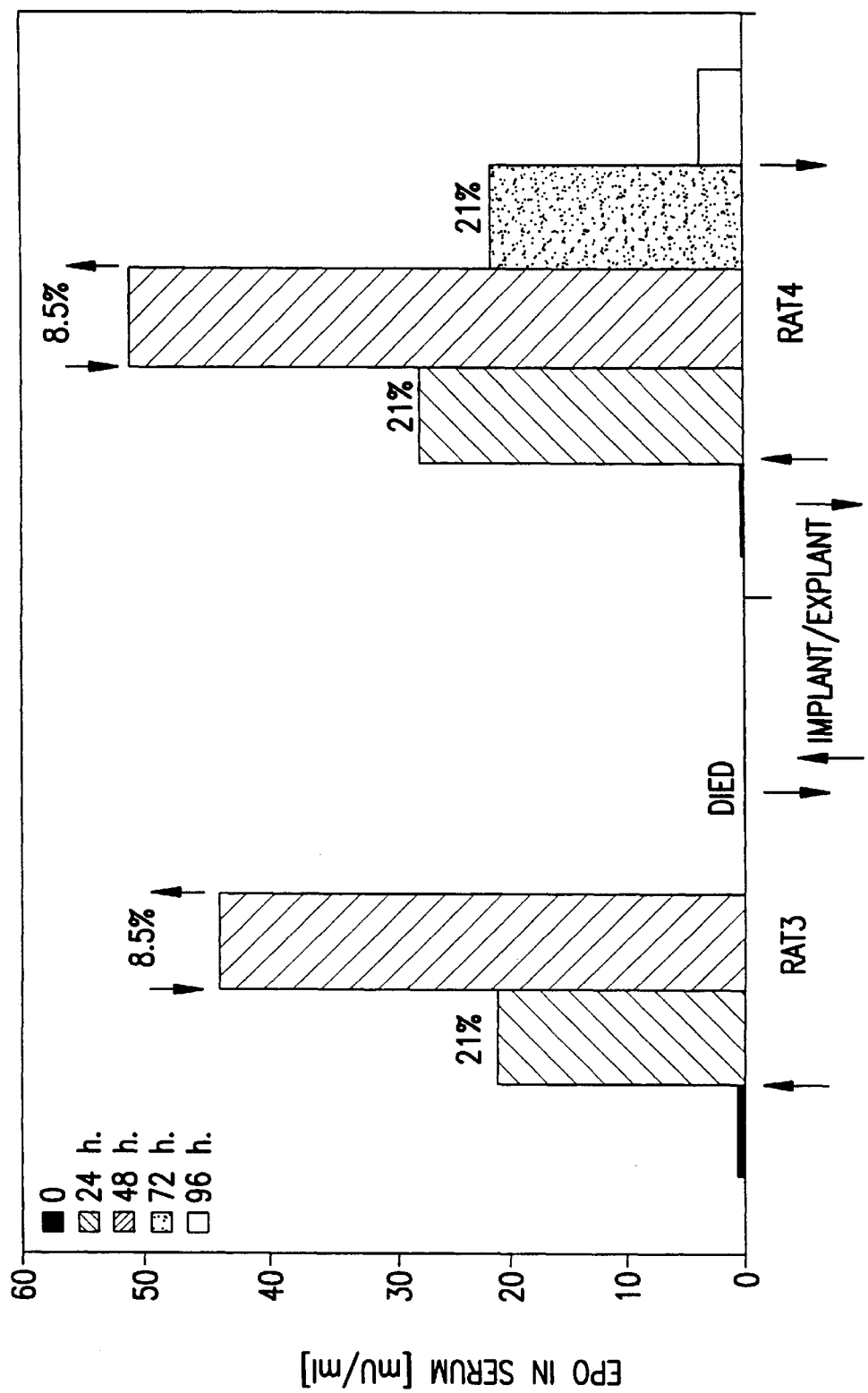
FIG. 7: In vivo regulation of human EPO production by encapsulated engineered myoblasts implanted into rats. The serum EPO levels (mUI/ml) are given two rats, over a 96 hour time frame, from prior to implant to post-explant. This figure shows the treatment experiment, in which the rats were exposed to normoxic oxygen conditions for 24 hours, then hypoxic oxygen conditions for 24 hours, and returned to normoxic conditions for 24 hours. The capsule was then explanted.

In the treatment group, rats were assayed for serum EPO levels before implant. Rats were then exposed to normoxic conditions for 24 hours after implant, then exposed to hypoxic conditions for 24 hours, returned to normoxic conditions for 24 hours, and finally the device was explanted. The results are shown in FIG. 7. As that Figure shows, serum EPO levels increased upon device implant, increased further under hypoxic conditions, returned to the normoxic serum level when rat 4 was re-exposed to normoxic conditions, and finally returned to the pre-implant value at device explant. Rat 3 showed the same trend as rat 4 initially, but died during the course of the experiment.

We claim:

1. A cell that produces at least 500 UI erythropoietin/$10^6$ cells/day under normoxic conditions and that is hypoxia responsive such that the level of erythropoietin production increases under hypoxic conditions.

2. The cell of claim 1 wherein the cell has been transfected with the PGK-1 (Phospho-glycerate Kinase-1) hypoxia response element.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: PGK-1
      hypoxia responsive element

<400> SEQUENCE: 1
gtcgtgcagg acgtgaca                                                18

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: PGK-1
      hypoxia responsive element tandem repeat

<400> SEQUENCE: 2
gtcgtgcagg acgtgacact cgcgtcgtgc aggacgtgac a                      41